United States Patent
Akahane

(10) Patent No.: US 6,539,172 B2
(45) Date of Patent: Mar. 25, 2003

(54) FLUID HEATING DEVICE AND CARTRIDGE FOR THE SAME

(75) Inventor: Shuya Akahane, Shiojiri (JP)

(73) Assignee: Kabushiki Kaisha Sanko, Nagano (JP)

( * ) Notice: Subject to any disclaimer, the term of this patent is extended or adjusted under 35 U.S.C. 154(b) by 0 days.

(21) Appl. No.: 09/772,915

(22) Filed: Jan. 31, 2001

(65) Prior Publication Data

US 2002/0181948 A1 Dec. 5, 2002

(51) Int. Cl.$^7$ .......................... A61F 7/00; A61M 37/00
(52) U.S. Cl. ....................... 392/470; 604/6.13
(58) Field of Search ................ 392/470; 604/4.01, 604/6.13

(56) References Cited

U.S. PATENT DOCUMENTS 3,640,283 A 2/1972 Bhatia et al.
4,705,508 A * 11/1987 Karnavas et al. ........... 604/113
5,245,693 A * 9/1993 Ford et al. .................. 392/470

FOREIGN PATENT DOCUMENTS

WO 95/03680 2/1995

* cited by examiner

Primary Examiner—Teresa Walberg
Assistant Examiner—Thor Campbell
(74) Attorney, Agent, or Firm—Birch, Stewart, Kolasch & Birch, LLP

(57) ABSTRACT

The cartridge of the present invention is capable of improving both of the heating efficiency and the flowing efficiency. The cartridge is capable of being detachably attached to a fluid heating device including a heater for heating a fluid to be transfused. In the cartridge, the fluid passes through a zigzag-shaped fluid path. A contact section is capable of contacting the heater and is made flat. A sectional shape of the zigzag-shaped fluid path, which is perpendicular to a flowing direction of the fluid, is formed into a polygonal shape. The fluid heating device of the present invention included the cartridge.

15 Claims, 5 Drawing Sheets

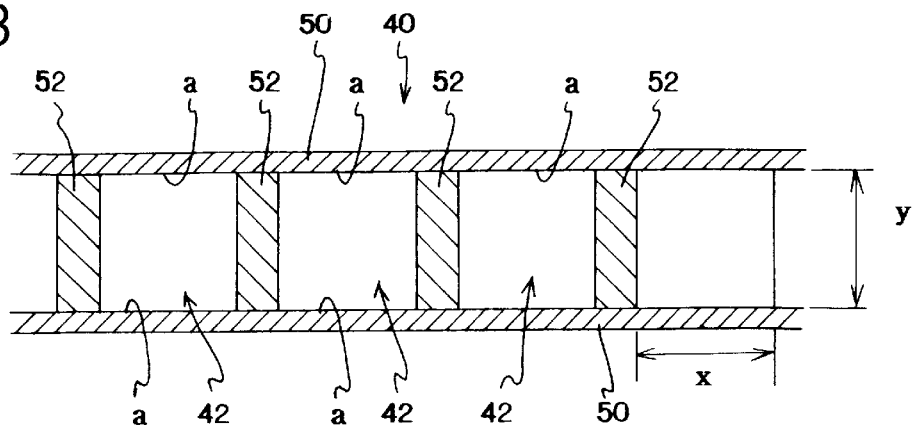
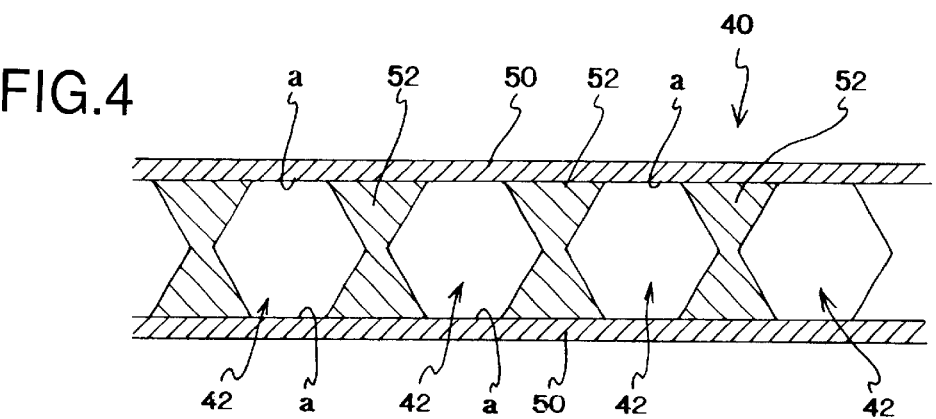
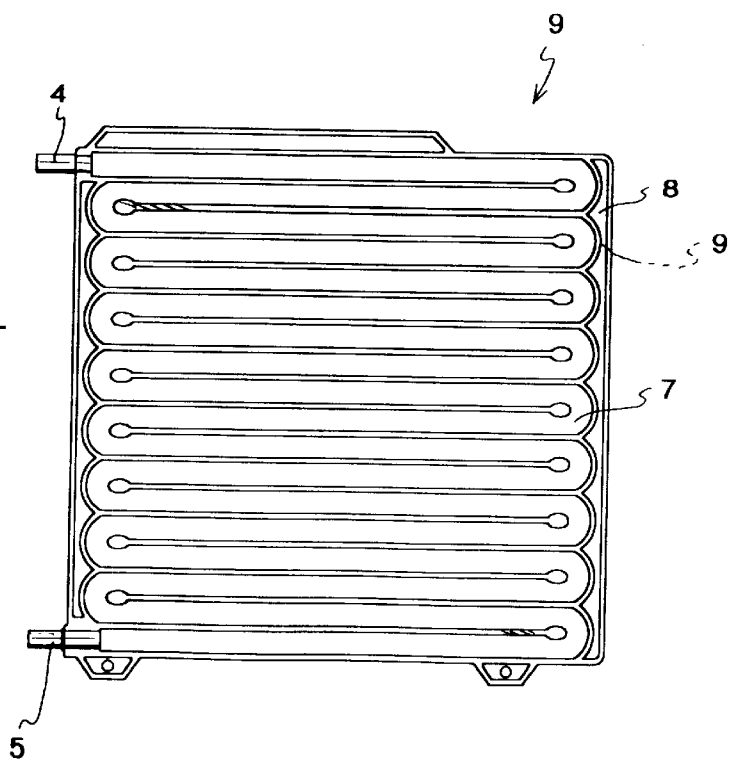
FIG.7 PRIOR ART

FLUID HEATING DEVICE AND CARTRIDGE FOR THE SAME

BACKGROUND OF THE INVENTION

The present invention relates to a fluid heating device, which is capable of frozen or cooled heating medical fluids, e.g., blood, liquid medicine, until reaching bodily temperature, and a cartridge, which can be detachably attached to the fluid heating device.

In the case of blood transfusion, blood, which has been cooled at temperature of 4–6° C., is usually used. If the cooled blood is transfused to a human body, the human body receives much stress.

On the other hand, if the temperature of the blood is higher than 42° C., cellular tissues of the blood are apt to be damaged.

Therefore, conventionally, medical fluids to be transfused to human bodies are heated to proper temperature, e.g., bodily temperature, by fluid heating devices.

Conventionally, blood is not directly passed through a fluid heating device. The fluid heating device has a cartridge, which is detachably attached to the fluid heating device and through which the blood is passed and heated. By employing the detachable cartridge, a body proper of the fluid heating device need not be washed and disinfected in spite of keeping sanitary conditions.

Conventional fluid heating devices are disclosed in Japanese Patent Gazettes No. 46-1945 and No. 9-500481.

The conventional fluid heating device disclosed in the Japanese Patent Gazette No. 46-1945 is shown in FIG. 7. A cartridge 9 is a sealed plastic container. The cartridge 9 is formed by assembling a pair of sub-members 8 and 9, and a zigzag fluid path 7 is formed in the cartridge 9. An outlet 4 and an inlet 5 are communicated to the zigzag fluid path 7.

The conventional fluid heating device disclosed in the Japanese Patent Gazette No. 9-500481 is shown in FIG. 8, which is an exploded perspective view. A cartridge 10 includes: a thin spacer 12, in which a zigzag fluid path 11 is formed; a pair of flexible heat conductive films 13, which are receptively adhered on an upper face and a lower face of the spacer 12 with adhesive means 15; and a frame 14 for holding the members 12 and 13.

The zigzag fluid path 11 is enclosed by the thin spacer 12 and the films 13, so the zigzag fluid path 11 is formed in the sheet-shaped cartridge.

When the cartridge 10 is attached to the fluid heating device, heaters (not shown), which are shaped to correspond to the zigzag shape of the path 11, respectively contact an upper face and a lower face of the cartridge 10 corresponding to the zigzag fluid path 11. With this structure, a medical fluid passing through the zigzag fluid path 11 can be heated.

If a sectional shape of the zigzag fluid path is a circular shape, friction between a medical fluid and an inner face of the zigzag fluid path can be small, so that the medical fluid can be flowed efficiently.

But heating efficiency is more important than the flowing efficiency. Thus, contact area between the heaters and the zigzag fluid path must be broader. The zigzag fluid path having the circular sectional shape is not advantageous to improve the heating efficiency.

Therefore, in the Japanese Patent Gazette No. 9-500481, the upper face and the lower face of the cartridge 10, which contact the heaters, are made flat so as to make the contact area broader. Namely, the sectional shape of the zigzag fluid path 11 is formed into a thin rectangle shape.

However, the conventional fluid heating devices have following disadvantages.

In the fluid heating device shown in FIG. 7, the sectional shape of the zigzag fluid path is the circular shape, so the heating efficiency is low.

In the fluid heating device shown in FIG. 8, the sectional shape of the zigzag fluid path the thin rectangle, so the friction between the medical fluid and the inner face of the zigzag fluid path is too great to efficiently pass the medical fluid. It takes a long time to pass the medical fluid through the cartridge.

SUMMARY OF THE INVENTION

An object of the present invention is to provide a cartridge, which is capable of improving both of the heating efficiency and the flowing efficiency.

Another object of the present invention is to provide a fluid heating device having the cartridge.

To achieve the objects, the present invention has following structures.

The cartridge of the present invention, which is capable of being detachably attached to a fluid heating device including a heater for heating a fluid to be transfused, comprises:

a zigzag-shaped fluid path, through which the fluid passes; and a contact section being capable of contacting the heater, the contact section being made flat, wherein a sectional shape of the zigzag-shaped fluid path, which is perpendicular to a flowing direction of the fluid, is formed into a polygonal shape.

In the cartridge of the present invention, the sectional shape of the zigzag-shaped fluid path is formed into the polygonal shape, so that the friction between the fluid and an inner face of the zigzag-shaped fluid path can be reduced and the flowing efficiency can be improved. Contact area of the contact section can be broader, so that the heating efficiency can be improved.

In the cartridge, the sectional shape of the zigzag-shaped fluid path may be formed into a regular square. With this structure, said friction in the zigzag-shaped fluid path can be lower than that in the zigzag-shaped fluid path having a rectangular cross section. Namely, the fluid can be efficiently flowed, and the contact area can be broader.

In the cartridge, area of a cross section of the zigzag-shaped fluid path, which is perpendicular to the flowing direction of the fluid, may be partially changed. With this structure, a turbulent flow of the fluid occurs at positions, at which the area of the cross section of the zigzag-shaped fluid path is changed, so that the fluid can be agitated and uniformly heated.

In the cartridge, the zigzag-shaped fluid path may be formed into a zigzag shape by a plurality of partitions, and width of the zigzag-shaped fluid path may be wider than that of the partitions. With this structure, the contact area can be broader without changing size of the cartridge. Further, heat conduction through the partitions can be made lower, so that the heating efficiency can be improved.

In the cartridge, the zigzag-shaped fluid path may be a zigzag-shaped through-hole, whose both ends are respectively opened in both sides of a cartridge body proper, and the both ends of the zigzag-shaped through-hole may be respectively covered with sheet-shaped members, which are capable of contacting the heater.

In the cartridge, the cartridge body proper and the sheet-shaped members may be molded with polycarbonate. With this structure, heat-deformation of the cartridge can be prevented.

In the cartridge, the sheet-shaped members may be transparent. With this structure, the fluid heated in the cartridge can be visually observed.

On the other hand, the fluid heating device of the present invention comprises:

a heater for heating a fluid to be transfused; and a detachable cartridge of the present invention.

In the fluid heating device of the present invention, the friction between the fluid and an inner face of the zigzag-shaped fluid path can be reduced and the flowing efficiency can be improved. Contact area of the contact section can be broader, so that the heating efficiency can be improved.

BRIEF DESCRIPTION OF THE DRAWINGS

Embodiments of the present invention will now be described by way of examples and with reference to the accompanying drawings, in which:

FIG. 3 is a sectional view of a zigzag-shaped fluid path having a regular square sectional shape;

FIG. 4 is a sectional view of the zigzag-shaped fluid path having a regular hexagonal sectional shape;

FIG. 7 is a sectional view of the conventional cartridge disclosed in the Japanese Patent Gazette No. 46-1945.

DETAILED DESCRIPTION OF THE PREFERRED EMBODIMENTS

Preferred embodiments of the present invention will now be described in detail with reference to the accompanying drawings.

Figure 1:
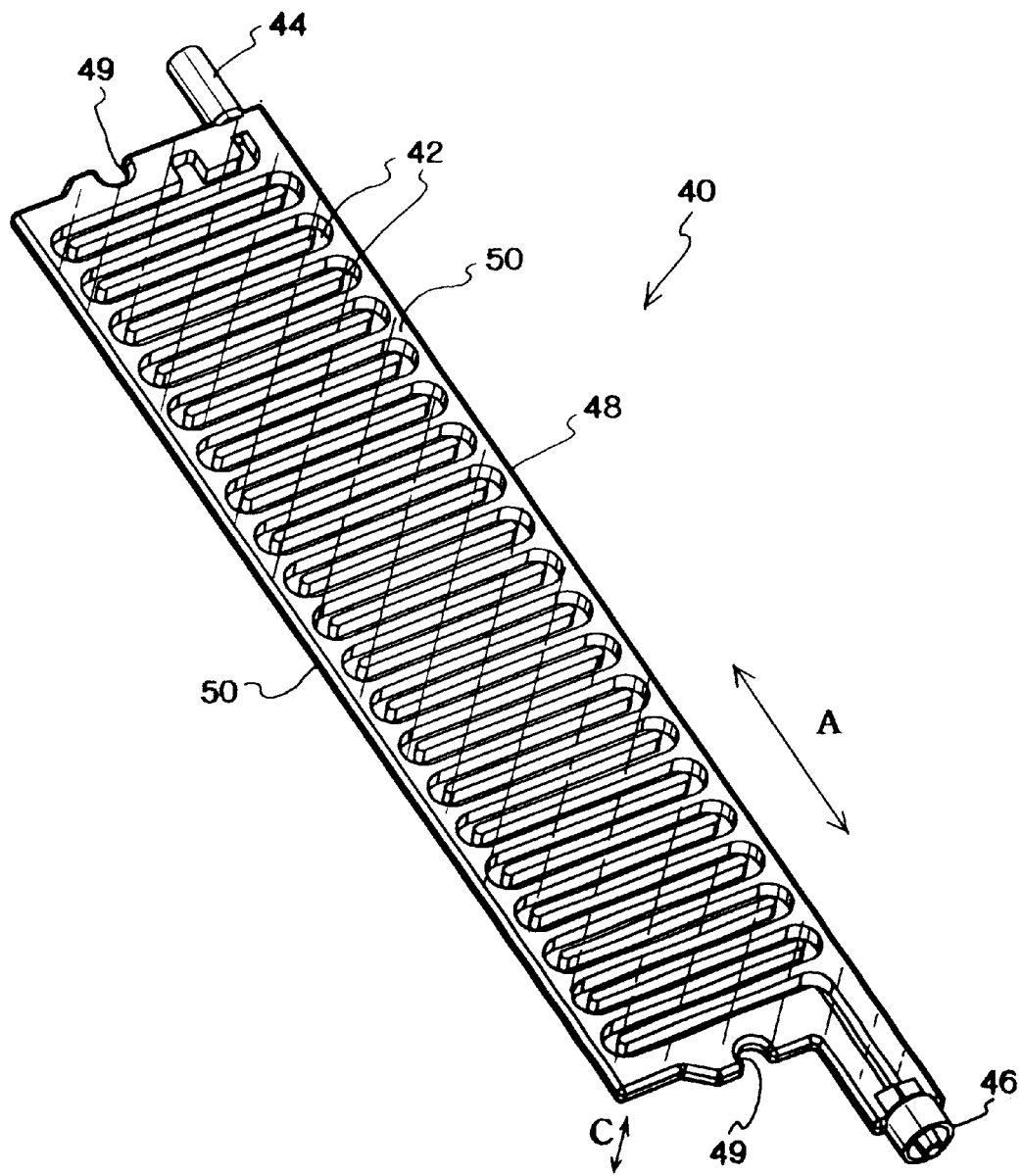
FIG. 1 is a perspective view of the cartridge of an embodiment of the present invention.
Figure 2:
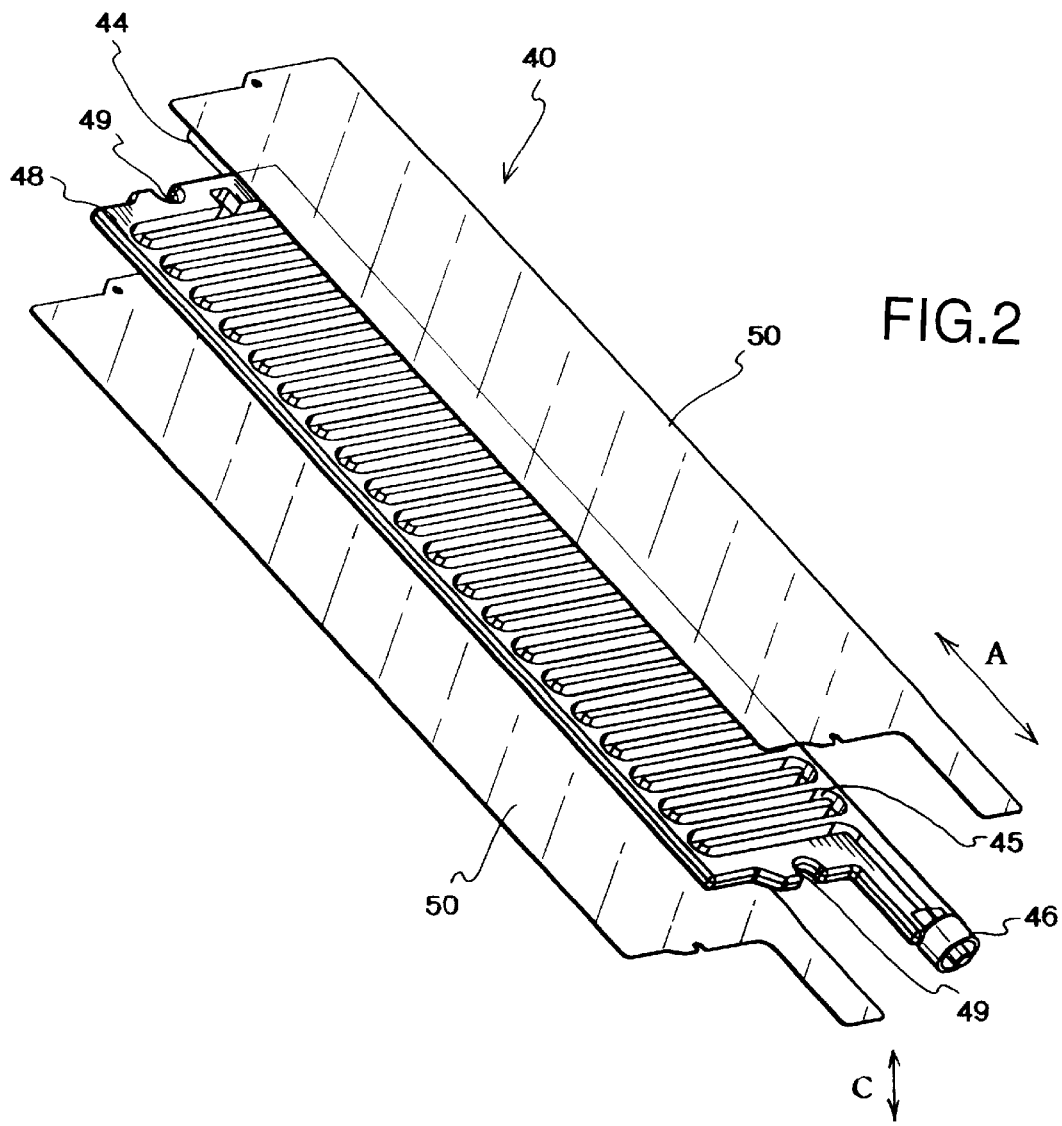
FIG. 2 is an exploded perspective view of the cartridge shown in FIG. 1.

Firstly, an embodiment of the cartridge of the present invention will be explained with reference to FIGS. 1 and 2.

The cartridge 40 has: a zigzag-shaped fluid path 42, through which a medical fluid, e.g., blood, passes and which winds with respect to the longitudinal direction of the cartridge 40; an inlet 44, to which the medical fluid to be heated is supplied; and an outlet 46, from which the heated medical fluid is discharged outside.

Figure 6:
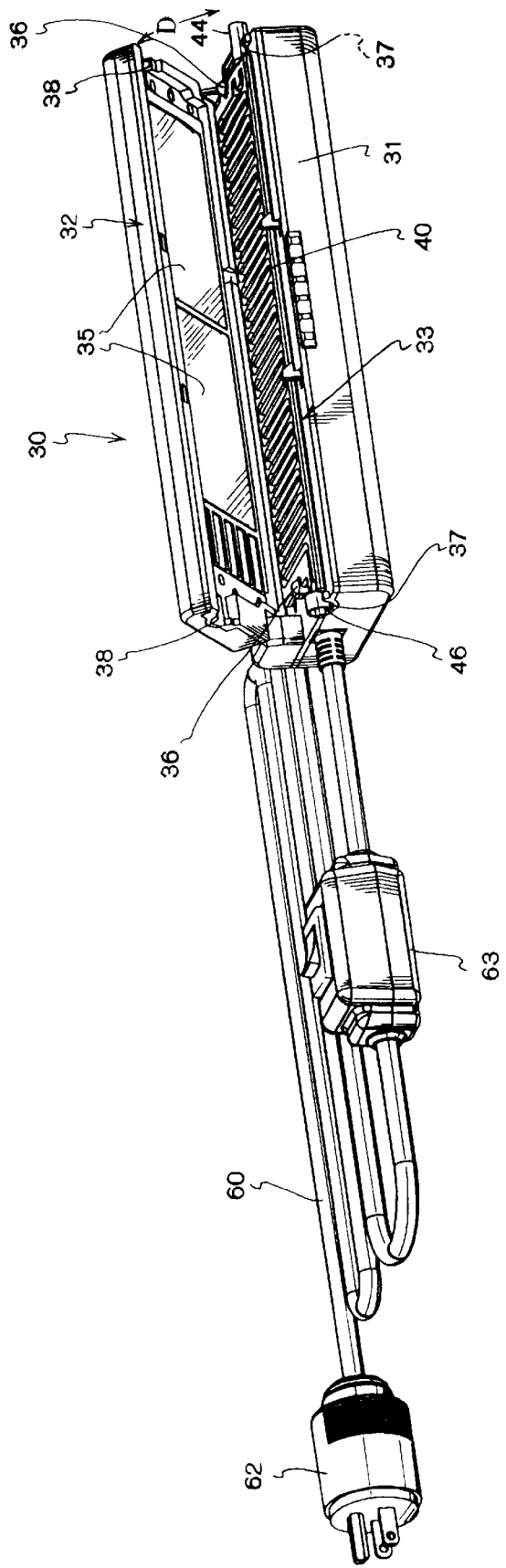
FIG. 6 is a perspective view of a fluid heating device to which the cartridge is attached.

The cartridge 40 can be detachably attached to a fluid heating device 30 (see FIG. 6).

A body proper 48 of the cartridge 40 includes a zigzag-shaped through-hole 45, which is bored in a direction of an arrow "C" and which winds with respect to the longitudinal direction "A" of the cartridge body proper 48. A pair of sheets 50 respectively are adhered on both faces of the cartridge body proper 48 so as to close both opening sections of the zigzag-shaped through-hole 45.

By closing both opening sections of the zigzag-shaped through-hole 45 with the sheets 50, the zigzag-shaped fluid path 42 is formed.

The cartridge body proper 48 is a thin rectangular plate.

One end of the zigzag-shaped through-hole 45 is communicated to the inlet 44, which introduces the medical fluid to the zigzag-shaped fluid path 42; The other end of the zigzag-shaped through-hole 45 is communicated to the outlet 46, from which the medical fluid is discharged outside.

The inlet 44 and the outlet 46 are formed as connectors based on ISO standard. Namely, tubes will be respectively connected to the inlet 44 and the outlet 46.

The cartridge body proper 48, the inlet 44 and the outlet 46 are molded as one piece.

A pair of the sheets 50 are respectively adhered on the both faces of the cartridge body proper 48 by heat welding.

Adhesive strength of the sheets 50 can be higher by heat welding. Though the adhesive strength is lower, the sheets 50 may be adhered by vibration welding, adhesive, etc.

The cartridge body proper 48 and the sheets 50 may be made of polycarbonate.

Melting point of the polycarbonate is high, and the polycarbonate has higher heat-resistively and lower air-transmissivity. So the polycarbonate is a desired material of the cartridge 40.

Further, the polycarbonate prevents deformation of the cartridge 40, which occurs when the cartridge 40 is heated.

Note that, the cartridge body proper 48 and the sheets 50 may be made of other plastic materials.

The polycarbonate body proper 48 may be molded by vacuum molding, pressure forming, blow molding, etc.

In the present embodiment, the polycarbonate body proper 48 was molded by injection molding. It can be efficiently molded by the injection molding.

Preferably, thickness of the sheets 50 is 0.5 mm or less. If the thickness is more than 0.5 mm, heat conductivity from heaters 35 (see FIG. 6) of the fluid heating device 30 to the medical fluid in the cartridge 40 is made lower, so that heating efficiency is also made lower.

Preferably, the sheets 50 are transparent sheet. By employing the transparent sheets 50, a color of the medical fluid, etc. can be visually observed.

Next, a sectional shape of the zigzag-shaped fluid path 42 will be explained with reference to FIG. 3.

Preferably, the sectional shape of the zigzag-shaped fluid path 42 is formed into a regular square. An upper side "a" and a lower side "a" of each regular square are capable of contacting the heaters 35.

The sectional shape of the zigzag-shaped fluid path 42 is the regular square, so width "x" of the zigzag-shaped through-hole 45 of the cartridge body proper 48 is equal to height "y" of partitions 52 (or thickness of the cartridge body proper 48). Note that, the zigzag-shaped fluid path 42 is formed into a zigzag shape by a plurality of the partitions 52.

Figure 8:
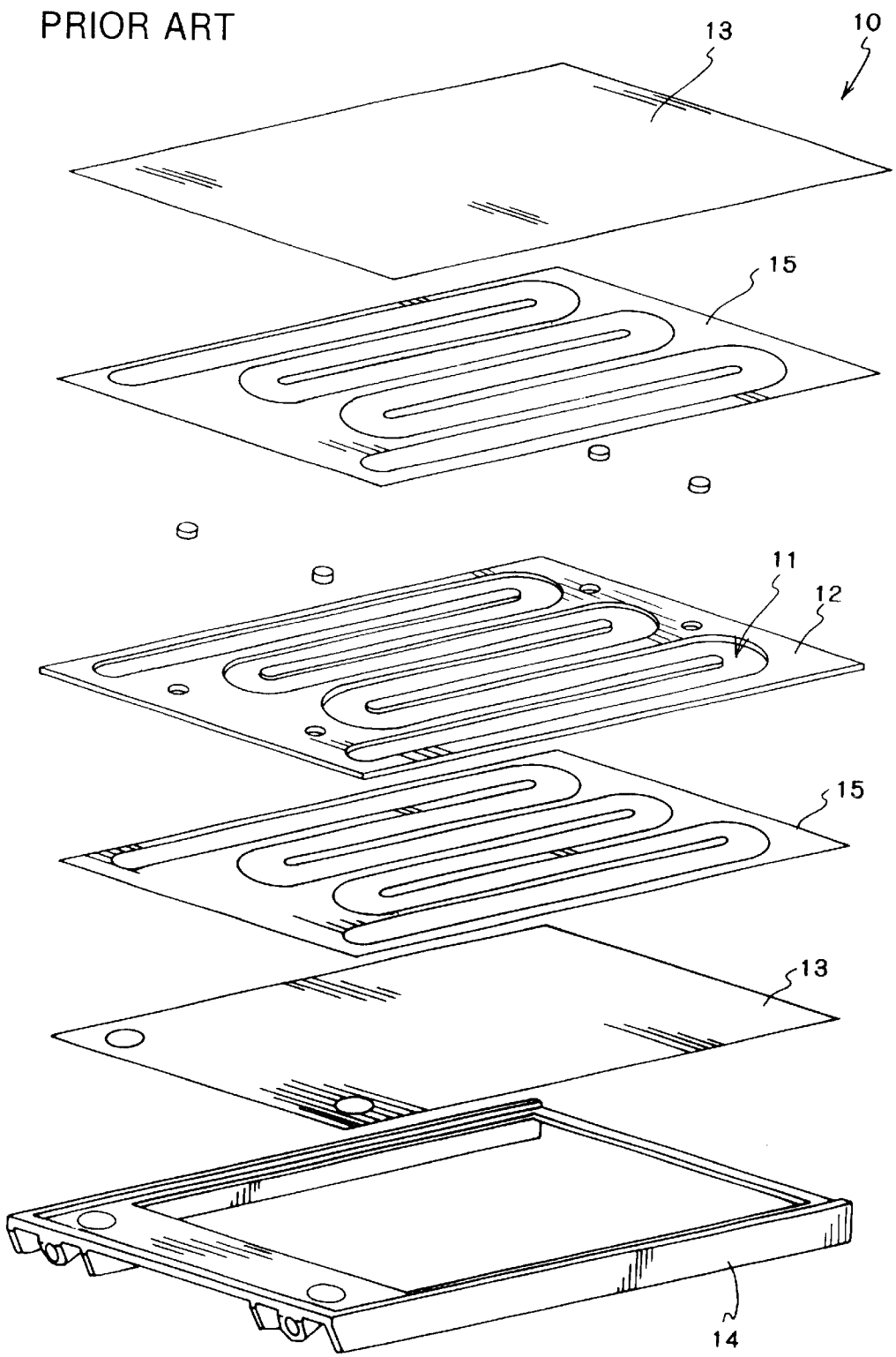
FIG. 8 is an exploded perspective view of the conventional cartridge disclosed in the Japanese Patent Gazette No. 9-500481.

In comparison with a zigzag-shaped fluid path having a circular cross section, friction between the medical fluid and an inner face of the zigzag-shaped fluid path 42 is greater; in comparison with a zigzag-shaped fluid path having a thin rectangular cross section (see FIG. 8), the friction in the zigzag-shaped fluid path 42 is smaller.

Unlike the zigzag-shaped fluid path having the circular cross section, total area of contact sections, which are capable of contacting the heaters 35, can be broader.

The zigzag-shaped fluid path 42 has the regular square cross section, so the cartridge 40 has following advantages: the friction between the medical fluid and the inner face of the zigzag-shaped fluid path 42 can be reduced, so that the flowing efficiency of the medical fluid can be improved; and contact area of the contact sections can be broader, so that the heating efficiency can be higher.

FIG. 4 shows another embodiment of the cartridge 40. The sectional shape of the zigzag-shaped fluid path 42 has a regular hexagonal sectional shape.

Figure 5:
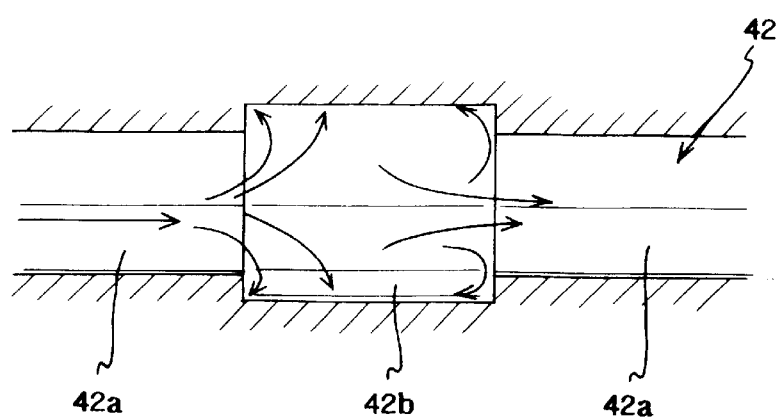
FIG. 5 is a sectional view of the zigzag-shaped fluid path having a regular octagonal sectional shape.

A preferable example of the zigzag-shaped fluid path 42 is shown in FIG. 5.

In FIG. 5, the zigzag-shaped fluid path 42 includes: parts 42a, each of which has the regular square cross section; and parts 42b, each of which has the circular cross section and is communicated to the adjacent parts 42a. In the present embodiment, an inner circular edge of the part 42b corresponds to a circumcircle of an inner square edge of the part 42a, and area of the circular cross section of the part 42b is broader than that of the square cross section of the part 42a.

As shown in FIG. 5, a flow of the medical fluid becomes a turbulent flow (see arrows) when the flow enters the part 42b from the part 42a, so that the medical fluid is agitated.

Further, the flow of the medical fluid becomes the turbulent flow when the flow enters the part 42a from the part 42b, so that the medical fluid is agitated again.

Even if the heaters 35 unevenly heats the medical fluid in the zigzag-shaped fluid path 42, temperature of the medical fluid can be made even by the agitation.

Note that, area of the square cross section of the part 42a may be broader than that of the circular cross section of the part 42b.

Means for agitating the medical fluid is not limited to the method of changing the cross sectional shape of the zigzag-shaped fluid path shown in FIG. 5.

Namely, area of the cross section of the zigzag-shaped fluid path 42, which is perpendicular to the flowing direction of the medical fluid, is partially changed. The zigzag-shaped fluid path 42 may be merely made wide and narrow.

When the area of the cross section is changed, the flow of the medical fluid becomes the turbulent flow, so that the medical fluid can be agitated. Therefore, temperature of the medical fluid can be made even by the agitation even if the heaters 35 unevenly heats the medical fluid.

Preferably, as shown in FIGS. 3 and 4, width of the partitions 52 is narrower than the width "x" of the zigzag-shaped fluid path 42.

With this structure, the contact area of the zigzag-shaped fluid path 42, which contacts the heaters 35, can be broader without changing size of the cartridge 40.

Further, heat conduction or heat leakage through the partitions 52 can be made lower, so that the heating efficiency can be improved.

Successively, the fluid heating device 30, to which the cartridge 40 is attached, will be explained with reference to FIG. 6.

The cartridge 40 is detachably attached to a box-shaped body 31 of the device 30.

A cover 32 is attached to the body 31 and can be moved in a direction of an arrow "D" so as to open and close the body 31. In FIG. 5, the cover 32 is opened, and the cartridge 40 is accommodated in an accommodating section 33 of the body 31.

A plurality of the planar heaters 35 are provided in the cover 32 and the accommodating section 33 of the body 31. Note that, the heaters 35 of the accommodating section 33 are located under the cartridge 40, so they are not shown in FIG. 5.

The heaters 35 are pressed onto the cartridge 40 when the cover 32 is closed. Namely, the heaters 35 are always biased toward the cartridge 40 by proper means, e.g., springs, (not shown).

Bosses 36 are projected toward the cover 32 from the body 31 so as to correctly position the cartridge 40. The bosses 36 respectively fit into engaging sections 49 of the cartridge 40. The engaging sections 49 are respectively formed at longitudinal ends of the cartridge 40 (see FIGS. 1 and 2).

When the cover 32 is opened, the cartridge 40 is attached into the accommodating section 33. The bosses 36 respectively fit into the engaging sections 49, so that the cartridge 40 can be easily correctly positioned.

Connector holding sections 37 are formed at both longitudinal ends of the body 31. The inlet connector 44 of the cartridge 40 and the outlet connector 46 can be respectively fitted in the connector holding sections 37. On the other hand, connector-holding sections 38 are formed at both longitudinal ends of the cover 32. The inlet connector 44 and the outlet connector 46 also can be respectively fitted in the connector holding sections 38. When the cover 32 is closed, the connector holding sections 37 and 38 form circular holes.

The connectors 44 and 46 of the cartridge 40 can be projected outward through the circular holes, which are formed by the connector holding sections 37 and 38. Further, the connector holding sections 37 and 38 also correctly position the cartridge 40 in the accommodating section 33.

A plug 62 is connected to an electric source. The plug 62 is electrically connected to the heaters 35 in the body 31 by an electric code 60.

A switch 63 is provided to the electric code 60.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A cartridge, which is capable of being detachably attached to a fluid heating device including a heater for heating a fluid to be transfused, comprising:

a zigzag-shaped fluid path, through which the fluid passes; and a contact section being capable of contacting the heater, said contact section being made flat and constructed of a material that is heat conducting and transparent, wherein a sectional shape of said zigzag-shaped fluid path, which is perpendicular to a flowing direction of the fluid, is formed into a polygonal shape with sides that are substantially equilateral.

2. The cartridge according to claim 1, wherein the sectional shape of said zigzag-shaped fluid path is formed into a regular square.

3. The cartridge according to claim 1, wherein area of a cross section of said zigzag-shaped fluid path, which is perpendicular to the flowing direction of the fluid, is partially changed.

4. The cartridge according to claim 1, wherein said zigzag-shaped fluid path is formed into a zigzag shape by a plurality of partitions, and width of said zigzag-shaped fluid path is wider than that of said partitions.

5. The cartridge according to claim 1,
wherein said zigzag-shaped fluid path is a zigzag-shaped through-hole, whose both ends are respectively opened in both sides of a cartridge body proper, and
wherein the both ends of said zigzag-shaped through-hole are respectively covered with sheet-shaped members, which are capable of contacting the heater.

6. The cartridge according to claim 5, wherein said cartridge body proper and said sheet-shaped members are molded with transparent polycarbonate enabling visual observation of said fluid.

7. The cartridge according to claim 1, wherein the sectional shape of said zigzag-shaped fluid path is formed into a regular hexagon.

8. A fluid heating device, comprising:
a heater for heating a fluid to be transfused; and
a cartridge being detachably attached, said cartridge including:
  a zigzag-shaped fluid path, through which the fluid passes; and
  a contact section contacting said heater and being made flat,
wherein a sectional shape of said zigzag-shaped fluid path, which is perpendicular to a flowing direction of the fluid, is formed into a polygonal shape with sides that are substantially equilateral.

9. The fluid heating device according to claim 8,
wherein the sectional shape of said zigzag-shaped fluid path is formed into a regular square.

10. The fluid heating device according to claim 8,
wherein area of a cross section of said zigzag-shaped fluid path, which is perpendicular to the flowing direction of the fluid, is partially changed.

11. The fluid heating device according to claim 8,
wherein said zigzag-shaped fluid path is formed into a zigzag shape by a plurality of partitions, and width of said zigzag-shaped fluid path is wider than that of said partitions.

12. The fluid heating device according to claim 8,
wherein said zigzag-shaped fluid path is a zigzag-shaped through-hole, whose both ends are respectively opened in both sides of a cartridge body proper, and
wherein the both ends of said zigzag-shaped through-hole are respectively covered with sheet-shaped members, which are capable of contacting the heater.

13. The fluid heating device according to claim 12, wherein said cartridge body proper and said sheet-shaped members are molded with transparent polycarbonate enabling visual observation of said fluid.

14. The fluid heating device according to claim 8, wherein the sectional shape of said zigzag-shaped fluid path is formed into a regular hexagon.

15. The fluid heating device according to claim 8, wherein said box-shaped body includes two bosses projected toward said cover from said box-shaped body for correctly positioning said cartridge.

* * * * *